United States Patent [19]

Ueyama

[11] 4,445,035
[45] Apr. 24, 1984

[54] EMISSION COMPUTED TOMOGRAPHY HAVING RADIAL POSITION CONTROL OF RADIATION DETECTOR

[75] Inventor: Akihide Ueyama, Tochigi, Japan

[73] Assignee: Tokyo Shibaura Denki Kabushiki Kaisha, Kawasaki, Japan

[21] Appl. No.: 265,243

[22] Filed: May 19, 1981

[30] Foreign Application Priority Data

Aug. 28, 1980 [JP] Japan ................ 55-118964

[51] Int. Cl.³ ............................................. G01T 1/20
[52] U.S. Cl. ........................................... 250/363 S
[58] Field of Search ................ 250/363 S; 378/11, 13

[56] References Cited

U.S. PATENT DOCUMENTS

| | | | |
|---|---|---|---|
| 3,432,660 | 3/1969 | Anger. | |
| 3,970,853 | 7/1976 | Kuhl et al. | |
| 4,057,726 | 11/1977 | Jaszczak. | |
| 4,204,123 | 5/1980 | Stoddart | 250/363 S |
| 4,368,389 | 1/1983 | Blum | 250/363 S |

Primary Examiner—Davis L. Willis
Attorney, Agent, or Firm—Finnegan, Henderson, Farabow, Garrett & Dunner

[57] ABSTRACT

An emission computed tomography wherein a radiation detector is rotated around a subject to detect radiation emitted from radioisotopes distributed in the subject and a distributing image of the radioisotopes in any section of the subject is reconstructed on the basis of the detected data, the emission computed tomography including detector-driving apparatus for moving the detector to or from the subject as the detector is rotated around the subject, at least one distance-measuring device, such as an ultrasonic transducer, for measuring the distance between the detector and subject at every rotative position of the detector, and apparatus responsive to the measured distance for controlling the detector-driving apparatus in order to adjust the distance between the detector and subject within a predetermined range.

6 Claims, 9 Drawing Figures

FIG. 1
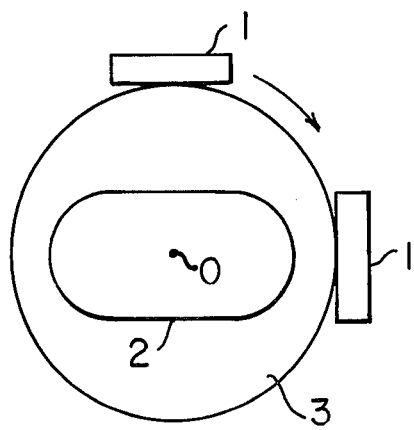
PRIOR ART
FIG. 3a
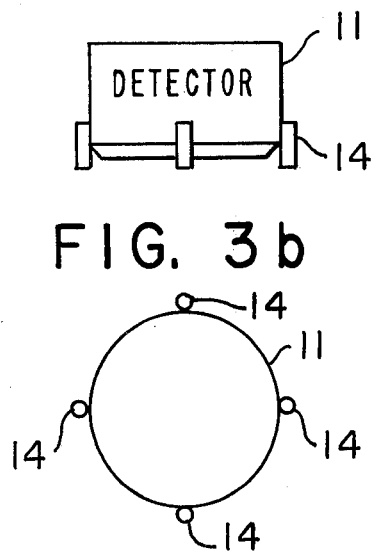
FIG. 3b
FIG. 2
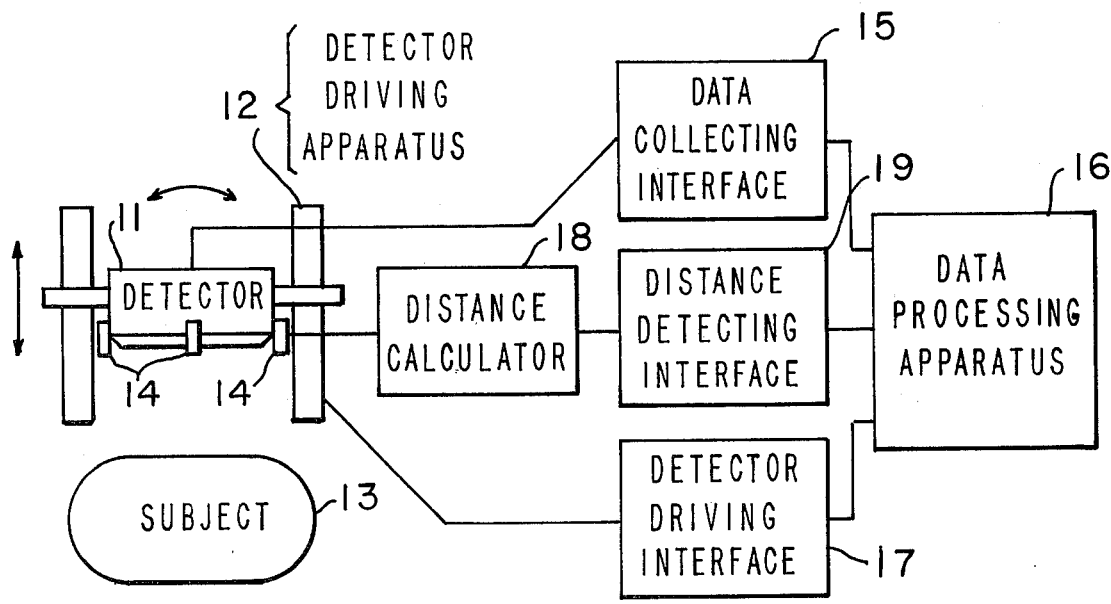

EMISSION COMPUTED TOMOGRAPHY HAVING RADIAL POSITION CONTROL OF RADIATION DETECTOR

BACKGROUND OF THE INVENTION

This invention relates to emission computed tomography and, more particularly, to emission computed tomography wherein γ-rays emitted from radioisotopes, distributed in a patient's body, are detected from a plurality of directions around the subject, and a radioisotope density distribution image on any section of the subject is reconstructed on the basis of the data obtained from the radioisotopes.

Conventional emission computed tomography, as shown in FIG. 1, includes a γ-ray detector 1 which rotates around a subject 2, ordinarily a patient's body, to detect γ-rays emitted from a plurality of directions so as to obtain projection images. In this case, the detector 1 is caused to move in a circular orbit 3 regardless of the sectional shape of the subject which, in this case for purposes of illustration, is substantially that of an ellipse. In the conventional apparatus, if the sectional shape of the subject is substantially an ellipse, the detector 1 in a circular orbit would be gradually withdrawn from the surface of the subject as the detector moves from the long axis to the short axis direction of the ellipse and approaches the surface of the subject from the short axis to the long axis direction of the ellipse. Therefore, since the detecting characteristics of the detector 1 tend to change with the rotating positions of the detector, it is impossible to obtain a projection image of well proportioned resolution. Additionally, the images obtained may be of inferior resolution since, when the detector 1 is in a position which is far from the surface of subject, the tomographic image reconstructed on the basis of the images will be of lower quality.

SUMMARY OF THE INVENTION

It is accordingly an object of this invention to improve the resolution of reconstructed images in emission computed tomography.

It is another object of the invention to provide emission computed tomography which can obtain projection images of well proportioned resolution at every rotative position of a detector.

It is yet another object of the invention to provide emission computed tomography wherein the detector can be rotated about a subject while maintaining a substantially constant distance between the detector and subject.

Briefly, these and other objects are achieved in accordance with the invention by constructing an emission computed tomography wherein a radiation detector is rotated around a subject to detect radiation emitted from radioisotopes distributed in the subject and an image of the radioisotopes in any section of the subject is reconstructed on the basis of the detected data, the emission computed tomography comprising detector-driving means for moving the radiation detector to or from the subject as the detector is rotated around the subject, distance-measuring means for measuring the distance between the detector and the subject at every rotative position of the detector, and means for controlling the detector-driving means in response to the distance between the detector and subject.

BRIEF DESCRIPTION OF THE DRAWINGS

FIG. 1 is a diagrammatic illustration for explaining the operation of conventional computed tomography;

FIG. 2 is a schematic block diagram to illustrate one embodiment of this invention;

FIG. 3(a) and (b) are respectively an elevational view and a plan view to illustrate detector and measuring devices for the apparatus of FIG. 2;

DESCRIPTION OF THE PREFERRED EMBODIMENT

Figure 4A:
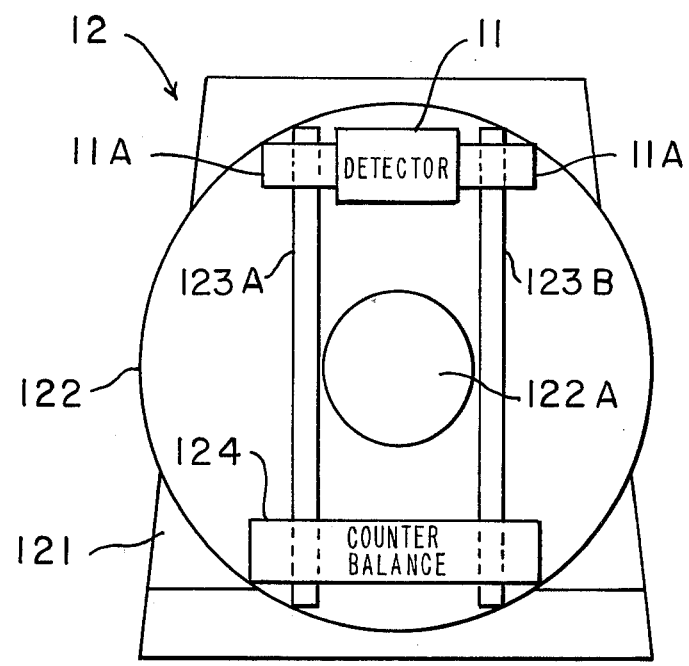
FIG. 4(a) and (b) are respectively an elevational view and a side view to illustrate a detector-driving apparatus of FIG. 2.
Figure 4B:
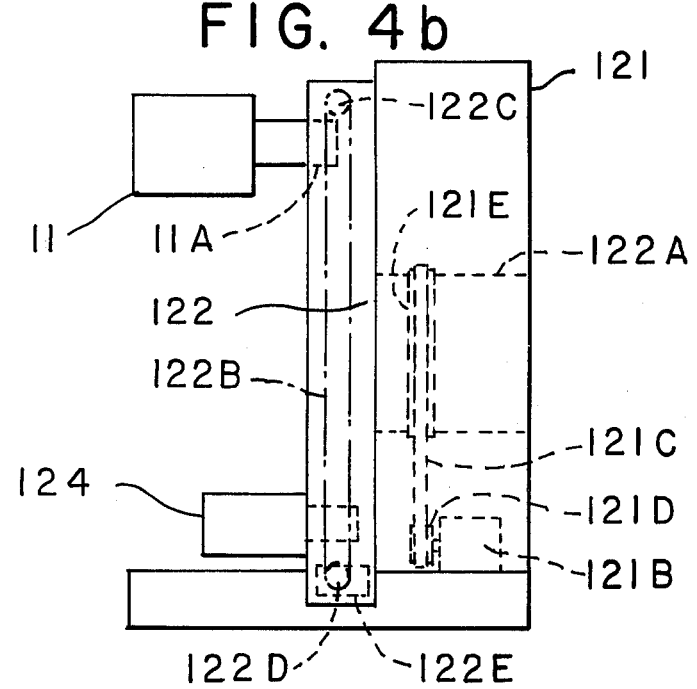

Referring to FIG. 2, an anger type gamma camera 11, acting as a detector of γ-rays, is rotated around a subject 13 and shifted in the diameter direction of its circular locus by a detector-driving apparatus 12. At least one distance-measuring device 14 (which is composed of, for example, sets of ultrasonic transmitters and receivers) issues an electrical detecting signal analogous to the distance between the detector 11 and the subject 13, as described more fully hereinafter. A data-collecting interface 15 applies the detecting signal from detector 11 to a data-processing apparatus 16. A detector-driving interface 17 controls the detector-driving apparatus 12. A distance-calculating circuit 18 actuates the ultrasonic transmitters of the measuring device 14 and then calculates the distance between the detector 11 and the subject 13 on the basis of the electric signal from the ultrasonic receiver of the distance-measuring device 14 which receives the ultrasonic echo signal reflected from the surface of the subject. A distance-detecting interface 19 controls an ultrasonic pulse generator (described later in detail) in the distance-calculating circuit 18 and supplies the distance data calculated by the distance-calculating circuit 18 to the data-processing apparatus 16.

As shown in FIGS. 3(a) and (b), for example, four ultrasonic distance-measuring devices 14 are attached on the circumference of the incidence aperture of the detector 11 at regular intervals and connected to the input terminal of the distance-calculating circuit 18 through lead wires (not shown). By such an arrangement of the distance-measuring devices 14, it is possible to measure precisely the distance between the detector 11 and the subject 13 without impairing the detecting function of the detector 11.

The detector-driving apparatus 12 is constructed, for example, as shown in FIGS. 4(a) and (b). That is, a ring 122 is rotatably mounted on a gantry 121 for supporting the detector-driving apparatus 12 through a shaft 122A. Two guide rails 123A and 123B are installed on the top surface of ring 122 at desired intervals and the detector 11 is attached at one end to a supporting rod 11A which is slidably set in the guide rails 123A and 123B. A counterbalance 124 is slidably set in the guide rails 123A, 123B at a position for countering the weight of the detector 11.

A driving motor 121B is disposed in the gantry 121 and coupled to the shaft 122A through a chain 121C supported on a sprocket 121D fixed on the rotating shaft of the motor 121B and a sprocket 121E fixed on the shaft 122A. A chain 122B is suspended between sprockets 122C and 122D which are rotatively mounted on the ring 122 respectively adjacent its upper and lower edges, as seen on the figures, and aligned with the detector 11 and the counterbalance 124. A part of the supporting rod 11A is fixed to the upper end of one leg of the chain 122B between the sprockets 122C, 122D and a part of the counterbalance 124 is fixed to the lower end of the other leg of the chain 122B. The lower sprocket 122D is coupled to the rotatable shaft of an up-down driving motor 122E, so that the detector 11 and counterbalance 124 are caused to shift up and down relatively when the motor 122E is alternately rotated in opposite directions for short periods.

Figure 5:
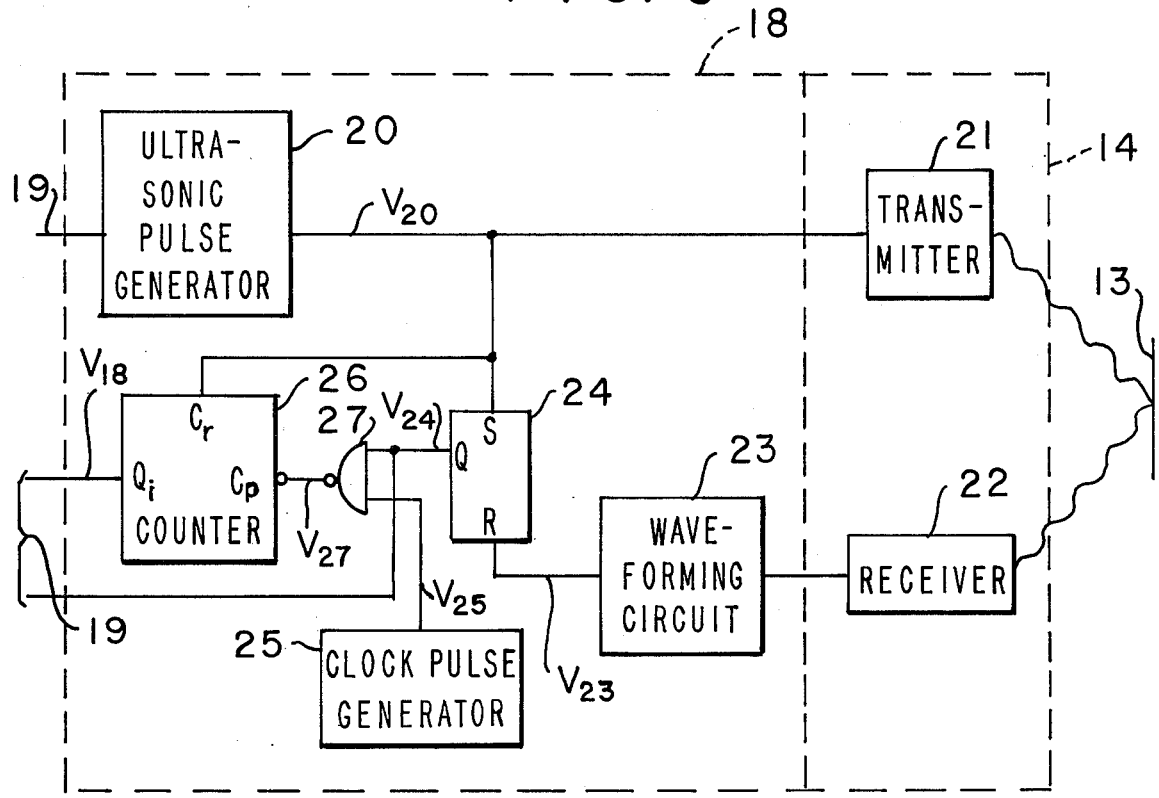
FIG. 5 is a schematic block diagram to illustrate a distance-calculating circuit for the apparatus of FIG. 2.

In FIG. 5, illustrating one concrete example of the distance-calculating circuit 18, an ultrasonic pulse generator 20 generates, upon receipt of a signal from the data processing apparatus 16, ultrasonic pulses to actuate the ultrasonic transmitting transducer 21 in the distance-measuring device 14. A wave-forming circuit 23 forms the signal waves from the ultrasonic receiving transducer 22 in the distance-measuring device 14. A flip-flop 24 is set by the output signal of the ultrasonic pulse generator 20 and reset by the output signal of the wave-forming circuit 23. A clock pulse generator 25 generates a clock pulse every unit time.

A counter 26 is cleared with the output signal of the ultrasonic pulse generator 20 and counts the output signals from a NAND gate 27 which has an input signal from the output of the set flip-flop 24 and from the output from the clock pulse generator 25. The counter 26 transmits a counting up output signal to the data processing apparatus 16 through the distance-detecting interface 19. Also, the output signal from the flip-flop 24 is supplied to the data processing apparatus 16 as a "busy38 flag, i.e., notice that distance is being measured, so that the operations of the data collecting and the shift of the detector will not interfere with each other.

The operation of the above-described apparatus will now be explained, referring also to FIGS. 6 and 7.

Figure 6:
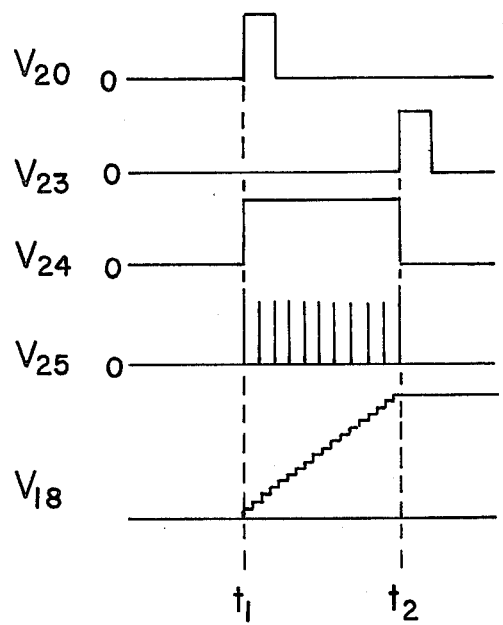
FIG. 6 and 7 are time charts for explaining the operation of the apparatus of FIG. 2.

First, referring to FIGS. 5 and 6, a controlling signal from the data processing apparatus 16 is sent to the distance-calculating circuit 18 through the distance-detecting interface 19 to generate the pulse signal V20 from the ultrasonic pulse generator 20. The flip-flop 24 is set by the pulse signal V20 and its output level rises to "1." At this time, since clock pulses V25 are generated from the clock pulse generator 25, signals corresponding to the clock pulses V25 are generated through the NAND gate 27 and the corresponding signals are applied to the counter 26 to gradually increase its output (time t1).

At the same time, ultrasonic sound waves are also initiated by the signal V20 from the ultrasonic pulse generator 20 and are emitted to the surface of the subject 13 from the ultrasonic transmitting transducer 21. The ultrasonic sound waves reflected from the surface of the subject are received by the ultrasonic receiving transducer 22 and applied to the reset terminal of the flip-flop 24 through the wave-forming circuit 23 as the signal V23 after conversion to electric signals. Therefore, the output V24 of the flip-flop 24 is inverted to "0" and the NAND gate 27 is closed.

Consequently, the counter 26 stops counting and is held at the counting value at the time of stopping (time t2). That is, the data corresponding to the distance of the detector 11 from the subject 13 can be obtained by counting the number of clock pulses which are generated in the time from the ultrasonic generating time (time t1) to the echo-detecting time (time t2). Such distance measurement is usually performed just before starting the data collection.

The measuring datum V18, obtained as described above, is sent to the data processing apparatus 16 through the distance-detecting interface 19 and the extent of the measured distance is judged by two predetermined threshold levels Vth1 and Vth2 to generate a detector-driving apparatus control signal V17.

Figure 7:
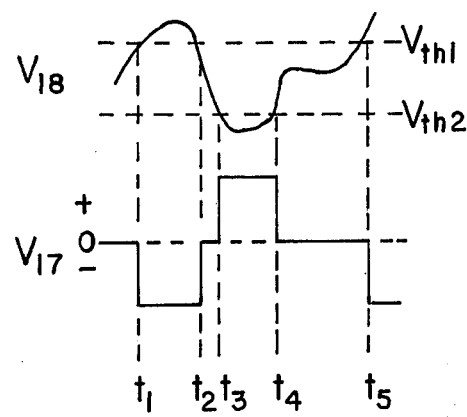

The proper distance of the detector from the subject 13 lies between the upper and lower thresholds Vth1 and Vth2, respectively, as shown in FIG. 7. When the locus of the detector 11, as shown by the measuring datum V18, exceeds the upper threshold level Vth1, the distance is too great and the data processing apparatus 16 issues a negative signal $-V17$ to the detector-driving apparatus 12. The up-down driving motor 122E is then operated to draw the detector 11 closer to the body of the subject.

On the other hand, when the locus of the detector 11, as shown by the measuring datum V18 falls below the lower threshold level Vth2, the distance is too close and the data processing apparatus issues a positive signal $+V17$ to the detector-driving apparatus 12. The up-down motor 122E is then operated to pull the detector 11 away from the body of the subject. As a result, whatever configuration the subject 13 offers, the detector 11 is kept an appropriate distance from the subject.

Moreover, the measurement of distance, the control of the detector-driving apparatus 12, according to the measuring result, and the following data collection are controlled so as not to interfere with each other by the timing control signals from the data processing apparatus 16. The ring 122 in the detector-driving apparatus 12 is also rotated under appropriate control signals.

This invention may be embodied in several forms without limitation to the embodiments described above. For example, the distance-measuring device may utilize laser beams as a substitute for the ultrasonic waves. The invention may also be adapted to use other circuits or apparatus having the same function as the constructions of the distance-calculating circuit and detector-driving apparatus, as illustrated. Also, although an anger type gamma camera is used as the detector in the embodiment as described, a polycrystalline detector may be used.

What is claimed is:

1. An emission computed tomography wherein a radiation detector is rotated around a subject to detect radiation emitted from radioisotopes distributed in the subject and a distributing image of the radioisotopes in any section of the subject is reconstructed on the basis of the detected data, the emission computed tomography comprising:

detector-driving means for moving the detector to or from the subject as the radiation detector is rotated around the subject;
   distance-measuring means for measuring the distance between the detector and the subject at every rotative position of the detector; and
   means responsive to said distance-measuring means for controlling said detector-driving means in order to adjust the radial distance between the detector and the subject.

2. The emission computed tomography of claim 1 wherein said controlling means adjusts said radial distance only to within a predetermined range.

3. The emission computed tomography of claim 2 wherein said radiation detector is mounted on a ring and wherein said detector-driving means comprise a gantry for rotatably supporting said ring, a detector-supporting member, at least one guide rail for slidably supporting said detector-supporting member thereon, and apparatus for selectably moving the detector-supporting member radially along the guide rail.

4. The emission computed tomography of claim 2 or 3 wherein said distance-measuring means comprise at least one distance-detecting element, means for calculating the distance between the detector and subject on the basis of the output from the element, and a distance-detecting interface for applying the output from said calculating means to said controlling means.

5. The emission computed tomography of claim 2 or 3 wherein said controlling means include data processing apparatus for receiving the output of the distance-detecting interface, comparing the output with the predetermined range, and issuing a positive or negative signal to said moving apparatus for moving the detector-supporting member toward or away from the subject, respectively.

6. The emission computed tomography of claim 4 wherein said distance-detecting element is an ultrasonic transducer element.

* * * * *